US009006491B2

(12) United States Patent
Ma et al.

(10) Patent No.: US 9,006,491 B2
(45) Date of Patent: Apr. 14, 2015

(54) STRUCTURE AND METHOD FOR SYNTHESIZING AND USING DIALKYL(2,4,6- OR 2,6-ALKOXYPHENYL)PHOSPHINE AND ITS TETRAFLUOROBORATE

(75) Inventors: Shengming Ma, Hangzhou (CN); Bo Lü, Hangzhou (CN); Chunling Fu, Hangzhou (CN)

(73) Assignee: Zhejiang University, Hangzhou (CN)

( * ) Notice: Subject to any disclaimer, the term of this patent is extended or adjusted under 35 U.S.C. 154(b) by 108 days.

(21) Appl. No.: 13/383,208

(22) PCT Filed: Dec. 21, 2009

(86) PCT No.: PCT/CN2009/001527
§ 371 (c)(1),
(2), (4) Date: Jan. 9, 2012

(87) PCT Pub. No.: WO2011/047501
PCT Pub. Date: Apr. 28, 2011

(65) Prior Publication Data
US 2012/0197030 A1 Aug. 2, 2012

(30) Foreign Application Priority Data
Oct. 22, 2009 (CN) .......................... 2009 1 0154029

(51) Int. Cl.
*C07F 9/50* (2006.01)
*B01J 31/24* (2006.01)
*C07D 307/58* (2006.01)
*C07F 9/54* (2006.01)
*C07B 37/04* (2006.01)

(52) U.S. Cl.
CPC ........... *B01J 31/2404* (2013.01); *C07D 307/58* (2013.01); *C07F 9/5022* (2013.01); *C07F 9/5442* (2013.01); *C07B 37/04* (2013.01); *B01J 2231/4227* (2013.01); *B01J 2231/4283* (2013.01); *B01J 2531/824* (2013.01)

(58) Field of Classification Search
CPC ........... C07F 9/5022; B01J 2531/0258; C08G 59/621
USPC ................................................ 568/8, 11, 17
See application file for complete search history.

(56) References Cited

U.S. PATENT DOCUMENTS 6,291,722 B1 * 9/2001 Li ................................ 568/642
6,307,087 B1 * 10/2001 Buchwald et al. ............ 558/388
6,867,310 B1 * 3/2005 Buchwald et al. ............ 549/453
7,223,879 B2 5/2007 Buchwald et al.

FOREIGN PATENT DOCUMENTS

CN 1745049 A 3/2006

OTHER PUBLICATIONS

Gary A. Molander et al., Organotrifluoroborates: Protected Boronic Acids That Expand the Versatility of the Suzuki Coupling Reaction, Acc. Chem. Res. 2007, vol. 40, pp. 275-286, U.S.A.
Zhiqiang Weng et al., Metal Unsaturation and Ligand Hemilability in Suzuki Coupling, Acc. Chem. Res. 2007, vol. 40, pp. 676-684, U.S.A.
Ruben Martin et al., Palladium-Catalyzed Suzuki-Miyaura Cross-Coupling Reactions Employing Dialkylbiaryl Phosphine Ligands, Acc. Chem. Res. Nov. 2008, vol. 41, No. 11, pp. 1461-1473, U.S.A.
Adam F. Littke et al., Palladium-Catalyzed Coupling Reactions of Aryl Chlorides, Angew. Chem. Int. Ed. 2002, vol. 41, pp. 4176-4211, WILEY-VCH Verlag GmbH & Co. KGaA, Weinheim.
David S. Surry et al., Biaryl Phosphane Ligands in Palladium-Catalyzed Amination, Angew. Chem. Int. Ed. 2008, vol. 47, pp. 6338-6361, WILEY-FCH Verlag GmbH & Co. KGaA, Weinheim.
Vladimir V. Grushin et al., Transformations of Chloroarenes, Catalyzed by Transition-Metal Complexes, Chem. Rev. 1994, vol. 94, pp. 1047-1062, U.S.A.
Henri Doucet, Suzuki-Miyaura Cross-Coupling Reactions of Alkylboronic Acid Derivatives or Alkyltrifluoroborates with Aryl, Alkenyl or Alkyl Halides and Triflates, Eur. J. Org. Chem., 2008, pp. 2013-2030, WILEY-VCH Verlag GmbH & Co. KGaA, Weinheim.
Brett P. Fors et al., "A Highly Active Catalyst for Pd-Catalyzed Amination Reactions: Cross-Coupling Reactions Using Aryl Mesylates and the Highly Selective Monoarylation of Primary Amines Using Aryl Chlorides," Journal of the American Chemical Society, vol. 130, No. 41, pp. 13552-13554 (Oct. 15, 2008).
Bo Lü et al., "Application of a readily available and air stable monophosphine HBF4 salt for the Suzuki coupling reaction of aryl or 1-alkenyl chlorides," Tetrahydron Letters, vol. 51, No. 9, pp. 1284-1286 (Mar. 1, 2010).
Bo Lü et al., "Application of Dicyclohexyl-(S)-trimethoxyphenyl Phosphine. HBF4 Salt for the Highly Selective Suzuki Coupling of the C-CI Bond in [beta]-Chlorobutenolides Over the More Reactive Allylic C-CO Bond," Chemistry-A European Journal, pp. 6434-6437 (May 5, 2010).

* cited by examiner

*Primary Examiner* — Sudhakar Katakam
*Assistant Examiner* — Pancham Bakshi
(74) *Attorney, Agent, or Firm* — Manni Li; Mei & Mark LLP

(57) ABSTRACT

The current invention relates to the structure, synthesis of dialkyl(2,4,6- or 2,6-alkoxyphenyl)phosphine or its tetrafluoroborate, as well as its applications in the palladium catalyzed carbon-chlorine bond activation for Suzuki coupling reactions and carbon-nitrogen bond formation reactions. The dialkyl(2,4,6- or 2,6-alkoxyphenyl)phosphine or its tetrafluoroborate could coordinate with the palladium catalyst to activate the inert carbon-chlorine bond highly selectively and catalyze Suzuki coupling reaction with arylboronic acid or carbon-nitrogen bond formation reaction with organic amines. The current invention uses only one step to synthesize dialkyl(2,4,6- or 2,6-alkoxyphenyl)phosphine and its tetrafluoroborate is stable in the air. Compared with known synthetic routes of ligands used in activating carbon-chlorine bonds, the method of current invention is short, easy to operate. Moreover, with this type of ligands, the Suzuki coupling products of optically active chlorolactones and arylboronic acids would maintain their configuration and optical purity.

17 Claims, No Drawings

STRUCTURE AND METHOD FOR SYNTHESIZING AND USING DIALKYL(2,4,6- OR 2,6-ALKOXYPHENYL)PHOSPHINE AND ITS TETRAFLUOROBORATE

CROSS-REFERENCE TO RELATED APPLICATIONS

The subject application is a U.S. national stage of PCT/CN2009/001527 filed on Dec. 21, 2009 and claims priority on Chinese application no. 200910154029.4 filed on Oct. 22, 2009. The contents and subject matter of the priority applications are incorporated herein by reference.

TECHNICAL FIELD

The current invention relates to the structure, a simple one step synthesis of dialkyl(2,4,6- or 2,6-alkoxyphenyl)phosphine or its tetrafluoroborate, as well as its applications in the Suzuki coupling reactions and the carbon-nitrogen bond formation reactions after palladium catalyzed carbon-chlorine bond activation reactions. To be more specific, during the synthesis of stable dialkyl(2,4,6- or 2,6-alkoxyphenyl)phosphine or its tetrafluoroborate, the highly active organic phosphine is used to coordinate with the palladium catalyst in order to activate the inert carbon-chlorine bond highly selectively.

BACKGROUND TECHNOLOGY

Organic halides are very important building blocks in organic synthesis. However, in their application in the past, expensive but relatively active organic bromides and iodides were used in coupling reactions to synthesize target molecules (*Chem. Rev.* 1994, 94, 1047). If inert carbon-chlorine bonds can be selectively activated and to use cheap chlorides in these types of reactions, it would be much better not only in respect of atom economy but also in respect of industrial cost. So far, some organic phosphine ligands can be used to activate inert carbon-chlorine bonds (*Angew. Chem. Int. Ed.* 2002, 41, 4176; *Acc. Chem. Res.* 2007, 40, 275; *Acc. Chem. Res.* 2007, 40, 676; *Acc. Chem. Res.* 2008, 41, 1461; *Eur. J. Org. Chem.* 2008, 2013; *Angew. Chem. Int. Ed.* 2008, 47, 6338). However, during the study on the carbon-chlorine bond coupling reactions of the optically active β-chloro-α,β-unsaturated five-membered lactones, the inventor of the current invention has discovered that some ligands commonly used in the activation of carbon-chlorine bonds (such as: tricyclohexylphosphonium tetrafluoroborate or 2-dicyclohexylphosphino-2',6'-dimethoxybiphenyl etc.) cannot yield the corresponding optically active coupling products highly selectively (please see embodiments for specific examples).

SUMMARY OF THE INVENTION

The object of the current invention is to provide a new type of organic phosphine ligand—dialkyl(2,4,6- or 2,6-alkoxyphenyl)phosphine and its tetrafluoroborate as well as the method of their preparation.

Another goal of the current invention is to provide a method and application for the inert $sp^2$ carbon-chlorine bonds activations highly selectively in the presence of the palladium catalyst and the above mentioned organic phosphine or its tetrafluoroborate.

The coordination of dialkyl(2,4,6- or 2,6-alkoxyphenyl)phosphine or its tetrafluoroborate with palladium catalyst can activate inert carbon-chlorine bonds highly selectively, and can catalyze Suzuki coupling reaction with arylboronic acid, or carbon-nitrogen bond formation reaction with organic amines. Compared with known synthetic routes of ligands used in activating carbon-chlorine bonds, the method of current invention is short, easy to operate, which has undoubtedly high research and application value.

The structures of the dialkyl(2,4,6- or 2,6-alkoxyphenyl)phosphine and its tetrafluoroborate of the current invention are as follows:

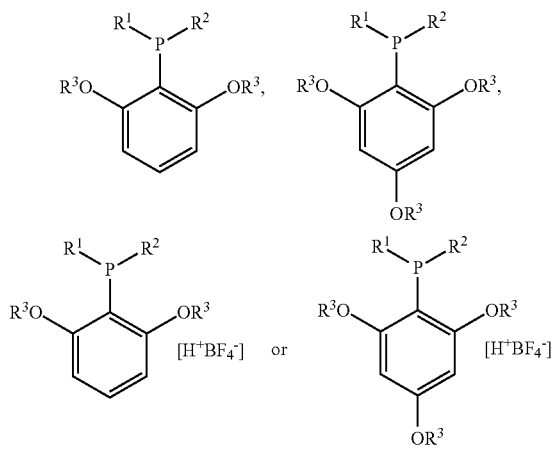

wherein, $R^1$, $R^2$ is isopropyl, tertbutyl, cyclopropyl, cyclopentyl, cyclohexyl or admantyl group and $R^3$ is alkyl group.

In the method to synthesize dialkyl(2,4,6- or 2,6-alkoxyphenyl)phosphine or its tetrafluoroborate of the current invention, trichlorophosphine, alkylmagnesium chloride, alkoxybenzene and n-butyl lithium are used as starting materials. 1,3- or 1,3,5-alkoxybenzene is reacted with n-butyl lithium in tetrahydrofuran to produce the corresponding lithium reagent. Alkylmagnesium chloride is reacted with trichlorophosphine to produce chlorodialkyl phosphine. The above mentioned lithium reagent is reacted with chlorodialkyl phosphine to produce dialkyl(2,4,6- or 2,6-alkoxyphenyl)phosphine. Tetrafluoroboric acid aqueous solution can be used to quench the reaction to produce the corresponding pure dialkyl(2,4,6- or 2,6-alkoxyphenyl)phosphine tetrafluoroborate after re-crystallization.

More detailed reaction steps are described as follows:

1) use tetrahydrofuran as an organic solvent, and at room temperature, alkoxybenzene $(R^3O)_nC_6H_{(6-n)}$ is reacted with n-butyl lithium for 2-15 hours to produce the corresponding lithium reagent $(R^3O)_nC_6H_{(5-n)}Li$;

2) react the lithium reagent above $(R^3O)_nC_6H_{(5-n)}Li$ with chlorodialkyl phosphine $R^1R^2PCl$ under -78-30° C. for 2 to 10 hours to produce a dialkyl(2,4,6- or 2,6-alkoxyphenyl)phosphine $(R^3O)_nC_6H_{(5-n)}PR^1R^2$, tetrafluoroboric acid aqueous solution is used to quench the reaction and to produce the corresponding dialkyl(2,4,6- or 2,6-alkoxyphenyl)phosphine tetrafluoroborate $((R^3O)_nC_6H_{(5-n)}PR^1R^2)(H^+BF_4^-)$; the molar ratio of said chlorodialkyl phosphine and (2,4,6- or 2,6-alkoxyphenyl) lithium is 0.8-1.2:1; said $R^1$, $R^2$ and $R^3$ are as described before. The reaction products can be purified by re-crystallization.

A typical reaction formula is as follows:

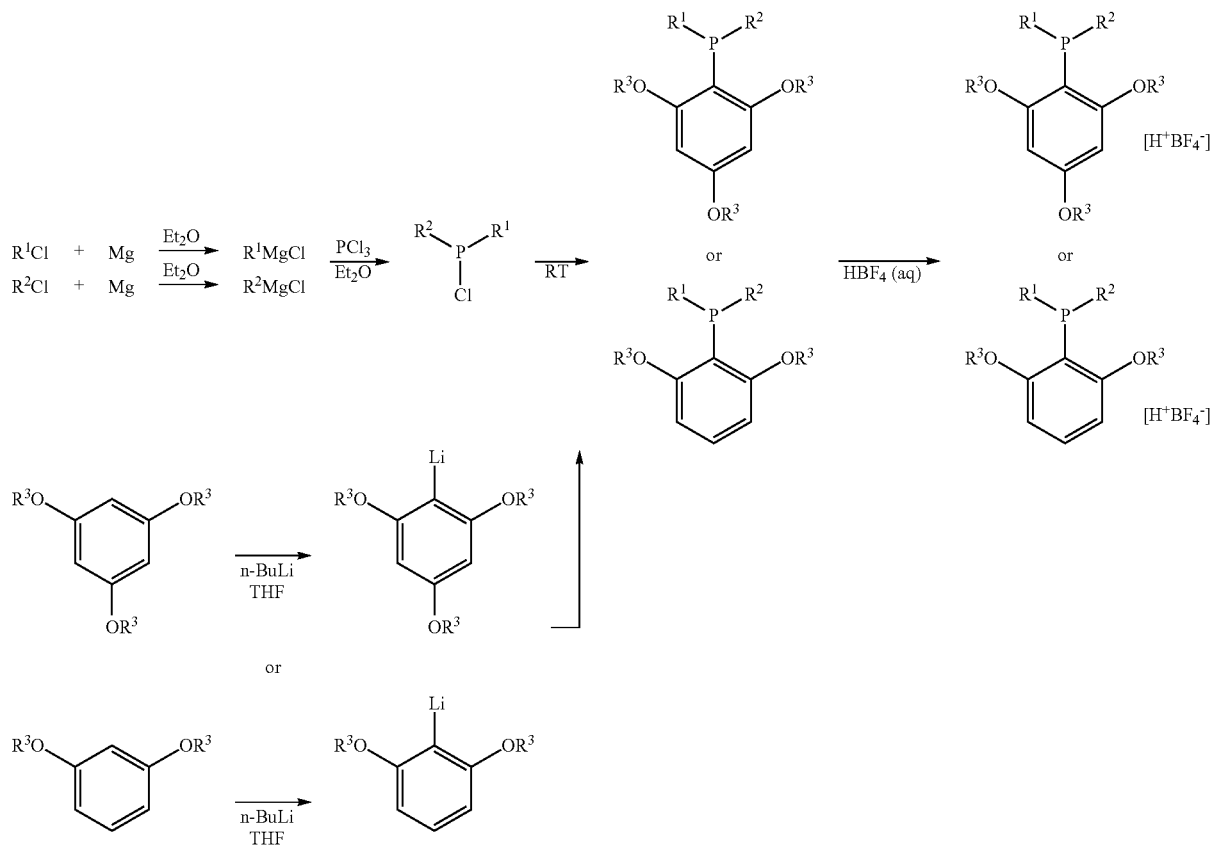

In the reaction, $R^1$, $R^2$ is isopropyl, tertbutyl, cyclopropyl, cyclopentyl, cyclohexyl or admantyl group and $R^3$ is alkyl group.

Dialkyl(2,4,6- or 2,6-alkoxyphenyl)phosphine and its tetrafluoroborate of the current invention can be used in the selective activation of inert carbon-chlorine bond for Suzuki coupling reaction to produce biphenyl compounds.

The more detailed description of the above mentioned application is as follows: The synthesis of the coupling compounds are carried out under the protection of inert gases, at 80-120° C., in an organic solvent, with the dialkyl(2,4,6- or 2,6-alkoxyphenyl)phosphine or its tetrafluoroborate and palladium as catalysts, arylboronic acid, base, water and arylchloride are reacted for 0.6-28 hours to produce the corresponding biphenyl compounds; said organic solvent is 1,4-dioxane or toluene; the equivalent molar ratio of base, palladium catalyst, dialkyl(2,4,6- or 2,6-alkoxyphenyl)phosphine or its tetrafluoroborate, arylboronic acid, water and arylchloride is 2.0~4.0:0.03~0.05:0.06~0.10:1.5~2.5:0~5.0: 1.0; said organic solvent is 1,4-dioxane or toluene; said base is potassium carbonate, potassium phosphate, cesium carbonate, or cesium fluoride; dialkyl(2,4,6- or 2,6-alkoxyphenyl)phosphine or its tetrafluoroborate is as claimed in claim 1; said arylchloride is $R^4$ substituted chlorobenzene; said arylboronic acid is $R^5$ substituted aryl boronic acid; $R^4$ is ortho-, meta-, para-substituted alkyl, alkoxy or hydrogen; $R^5$ is ortho-, meta-, para-substituted alkyl, alkoxy, aryl or hydrogen.

Alternatively, the synthesis of the coupling compounds is carried out under the protection of inert gases, the reaction temperature is 80-120° C., toluene is the solvent, palladium acetate, dialkyl(2,4,6- or 2,6-alkoxyphenyl)phosphine or its tetrafluoroborate, potassium carbonate, arylboronic acid and optically active chlorolactone undergo reaction for 5-60 minutes and the corresponding coupling optically active lactone compounds are obtained; the equivalent molar ratio of said palladium acetate, dialkyl(2,4,6- or 2,6-alkoxyphenyl)phosphine or its tetrafluoroborate, potassium carbonate, arylboronic acid and optically active chlorolactone is 0.05:0.05~0.10:3.0~4.5:1.2~2.0:1.0; the organic phosphine or its salt is the dialkyl(2,4,6- or 2,6-alkoxyphenyl)phosphine or its tetrafluoroborate of claim 1; the arylboronic acid is $R^5C_6H_4B(OH)_2$; the chemical structure of the optically active chlorolactone is

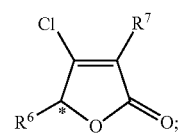

the chemical structure of the product coupled by optically active chlorolactone and aryl boronic acid is

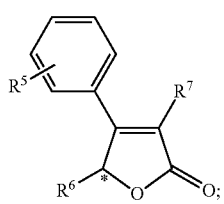

$R^5$ is ortho-, meta-, para-substituted alkyl, alkoxy, aryl or hydrogen; $R^6$ is alkyl, phenyl or heterocyclic group; $R^7$ is alkyl group; said heterocyclic group is thiophene, furan or pyridine; * is optically active carbon.

The typical method to synthesize Suzuki coupling compounds can be demonstrated by the following reaction formulas:

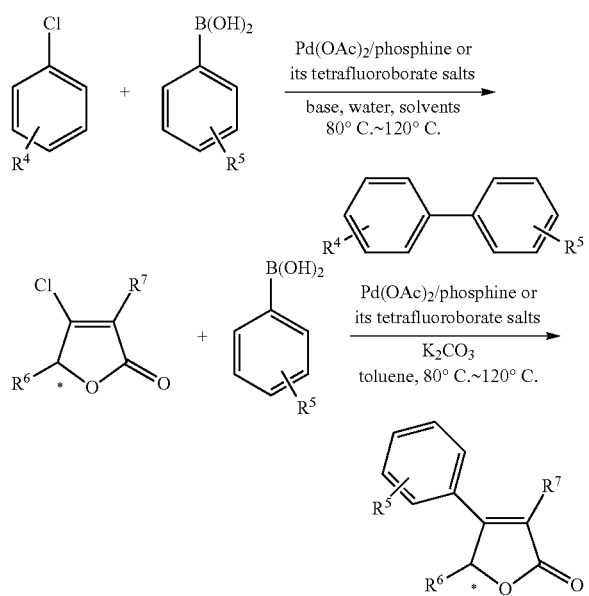

wherein $R^5$ is ortho-, meta-, para-substituted alkyl, alkoxy, aryl or hydrogen; $R^6$ is alkyl, phenyl or heterocyclic group; said heterocyclic group is thiophene, furan or pyridine; $R^7$ is alkyl group; said base is potassium carbonate, potassium phosphate, cesium carbonate, or cesium chloride; said organic phosphine is the dialkyl(2,4,6- or 2,6-alkoxyphenyl) phosphine.

Dialkyl(2,4,6- or 2,6-alkoxyphenyl)phosphine or its tetrafluoroborate of the current invention can also be used in the carbon-nitrogen bond formation reaction between the inert carbon-chloride bond and the amines to produce aromatic secondary amines or tertiary amines.

In other words, the synthesis of said aromatic secondary or tertiary amines is carried out under the protection of inert gases, toluene is the solvent, dialkyl(2,4,6- or 2,6-alkoxyphenyl)phosphine or its tetrafluoroborate and palladium are the catalysts, base, organic amines and aryl chlorides undergo reaction for 1-36 hours to obtain the corresponding coupling compounds of aromatic secondary or tertiary amines; the molar ratio of said base and palladium catalysts, organic phosphine or its tetrafluoroborate, organic amine and aryl chlorides is 1.5~4.0:0.01~0.05:0.015~0.10:1.2~2.5:1.0; said organic solvent is 1,4-dioxane or toluene; said palladium catalyst is palladium acetate or tris(dibenzylideneacetone) dipalladium ($Pd_2(dba)_3 \cdot CHCl_3$); base is potassium tert-butoxide, sodium tert-butoxide, potassium phosphate, potassium hydroxide, sodium hydroxide, sodium hydride, and the base which can provide alkoxy anion, hydrogen anion or hydroxyl anion; the organic phosphine or its salt is the dialkyl (2,4,6- or 2,6-alkoxyphenyl)phosphine or its tetrafluoroborate of claim 1; said aryl chloride is $R^4$ substituted chlorobenzene; said organic amine is $R^8$, $R^9$ substituted organic primary amine and secondary amine; $R^8$ is alkyl, phenyl or heterocyclic group; $R^9$ is alkyl, phenyl, heterocyclic group or hydrogen; said heterocyclic group thiophene, furan or pyridine.

The typical method to produce carbon-nitrogen coupling compounds can be demonstrated with the following formula:

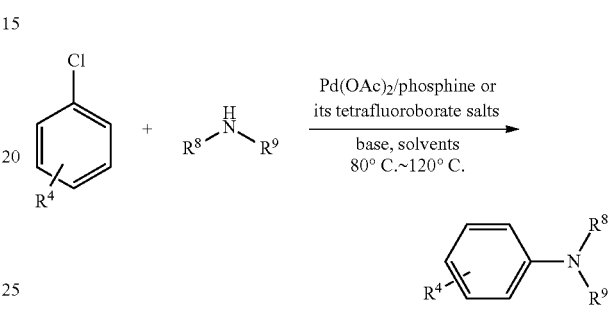

According to the method to synthesize biphenyl compounds of the current invention, dialkyl(2,4,6- or 2,6-alkoxyphenyl)phosphine or its tetrafluoroborate, potassium phosphate, palladium acetate, arylboronic acid and arylchloride are used as starting materials. Toluene or 1,4-dioxane is used as solvent. dialkyl(2,4,6- or 2,6-alkoxyphenyl)phosphine or its tetrafluoroborate is used to coordinated with palladium catalyst in order to activate inert carbon-chlorine bonds highly selectively to produce biphenyl compounds. The detailed steps are: 3.5 equivalent of anhydrous potassium phosphate powder is added into the reactor. The reactor is heated under vacuum and backfilled with inert gas for three times. After the reactor is cooled to room temperature, 0.03 equivalent of palladium acetate, 0.06 equivalent of dialkyl(2, 4,6- or 2,6-alkoxyphenyl)phosphine or its tetrafluoroborate, 2.0 equivalent of acrylboronic acid, 3.0 equivalent of water, 2.0 equivalent of arylchloride and 1 mL of 1,4-dioxane are added into the reactor. The reaction is carried out at 110° C. and the reactants are stirred for 0.6-28 hours to afford corresponding biphenyl compounds.

The method to produce optically active lactone compounds is as follows: dialkyl(2,4,6- or 2,6-alkoxyphenyl)phosphine or its tetrafluoroborate, potassium carbonate, palladium acetate, arylboronic acid and optically active chlorolactone are used as starting materials. Toluene is solvent. Dialkyl(2, 4,6- or 2,6-alkoxyphenyl)phosphine or its tetrafluoroborate is used to coordinated with palladium catalyst to activate inert carbon-chlorine highly selectively to produce optically active lactones. The synthesis steps are as follows: with the protection of inert gas, 0.05 equivalent of palladium acetate, 0.05-0.10 equivalent of dialkyl(2,4,6- or 2,6-alkoxyphenyl)phosphine or its tetrafluoroborate, 3.0-4.5 equivalents of potassium carbonate, 1.5 equivalents of arylboronic acid, optically active chlorolactone and toluene are added to the reactor. The reaction is carried out at 110° C. and the reactants are stirred for 5-60 minutes to afford the corresponding coupling optically active lactones.

The method to produce phenylamine of the current invention is as follows: dialkyl(2,4,6- or 2,6-alkoxyphenyl)phosphine or its tetrafluoroborate, potassium tert-butoxide, tris (dibenzylideneacetone)dipalladium (Pd$_2$(dba)$_3$CHCl$_3$) or palladium acetate, organic amine and arylchloride are used as starting materials. Toluene is used as the solvent. Dialkyl(2,4,6- or 2,6-alkoxyphenyl)phosphine or its tetrafluoroborate is used to coordinated with palladium catalyst to activate inert carbon-chlorine bonds highly selectively in order to produce aromatic secondary amines or tertiary amines. The steps are as follows: Under the protection of inert gases, 0.05 equivalent of palladium acetate, 0.075 equivalent of dialkyl(2,4,6- or 2,6-alkoxyphenyl)phosphine or its tetrafluoroborate, potassium tert-butoxide, arylchloride and toluene are added into the reactor. The reactants are stirred for 1-36 hours at 110° C. to afford the corresponding coupling aromatic secondary amines or tertiary amines.

The current invention relates to a new method to synthesize dialkyl(2,4,6- or 2,6-alkoxyphenyl)phosphine or its tetrafluoroborate, and its application in the inert carbon-chlorine bond activation for Suzuki coupling reactions and the carbon-nitrogen bond formation reactions. To be more specific, the current invention relates to a new method to synthesize dialkyl(2,4,6- or 2,6-alkoxyphenyl)phosphine or its tetrafluoroborate which is stable in the air, and to use the highly active organic phosphine ligand in the reaction to coordinated with palladium catalyst in order to activate sp$^2$ carbon-chlorine bonds highly selectively and to catalyze the Suzuki couplings with aryl boronic acids or carbon-nitrogen bond couplings with amines. The organic phosphine compounds of the current invention can be used in the Suzuki coupling reactions of optically active β-chloro-α,β-unsaturated five-membered lactones to produce the corresponding optically active products. However, two well-known organic phosphine (tricyclohexylphosphonium tetrafluoroborate and 2-dicyclohexylphosphino-2',6'-dimethoxybiphenyl) always used in carbon-chlorine bond activation would lead to racemizations.

The current invention uses only one step to synthesize dialkyl(2,4,6- or 2,6-alkoxyphenyl)phosphine and its tetrafluoroborate which are stable in the air, and develops a new type of organic phosphine compounds (dialkyl(2,4,6- or 2,6-alkoxyphenyl)phosphine and its tetrafluoroborate) which has been used in highly efficient activation of inert carbon-chlorine bonds and the applications in the inert carbon-chlorine bond for Suzuki coupling reactions and carbon-nitrogen bond formation reactions. Compared with known synthetic routes of ligands in activating carbon-chlorine bonds, the method of the current invention is short, easy to operate. Moreover, with this type of ligands, the Suzuki coupling products of optically active chlorolactones and arylboronic acids would maintain their configuration and optical purity.

DETAILED DESCRIPTION AND EMBODIMENTS

The following examples serve only to provide a better understanding of the invention without any limitation of the current invention.

Example 1

Synthesis of dicyclohexyl(2,4,6-trimethoxyphenyl)phosphine

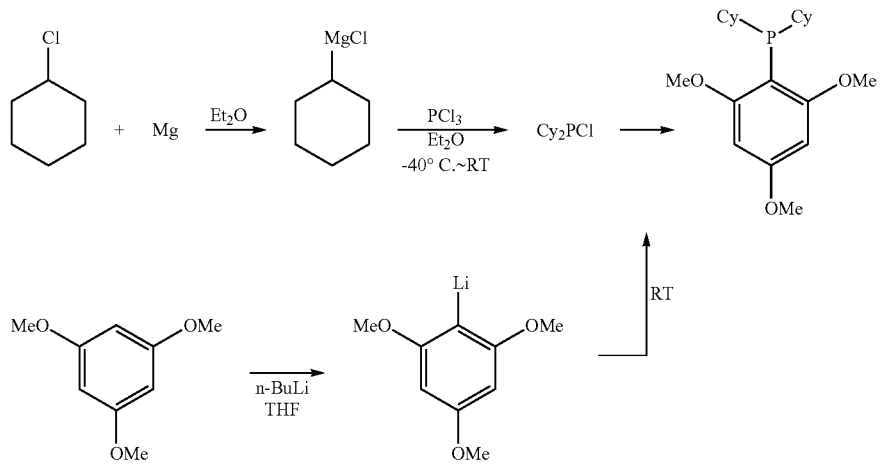

To a solution of trimethoxybenzene (1.0062 g, 6 mmol) in 20 mL of dry THF was added n-butyl lithium (2.6 mL, 2.5 M in hexane, 6.6 mmol) dropwise under N$_2$. The mixture was stirred for 4.5 hours at room temperature, at which time the reaction system was then cooled to −78° C. Chlorodicyclohexyl phosphine was added dropwise. After the mixture is stirred for 30 minutes, the reaction system was warmed up to room temperature and stirred for another 18 hours. Extraction with ethyl acetate, washed with water, dried over anhydrous sodium sulfate, and purified by column chromatography (petroleum ether/ethyl acetate=10/1~5/1) afforded 0.5514 g of product. The yield is 25%.

$^1$H NMR (300 MHz, CDCl$_3$) δ 6.08 (d, J=1.5 Hz, 2H). 3.81 (s, 3H), 3.77 (s, 6H), 2.30-2.16 (m, 2H), 1.92-1.54 (m, 8H), 1.48-0.90 (m, 12H); $^{31}$P NMR (121 MHz, CDCl$_3$) δ-14.6.

Example 2

Synthesis of dicyclohexyl(2,4,6-trimethoxyphenyl)phosphine tetrafluoroborate

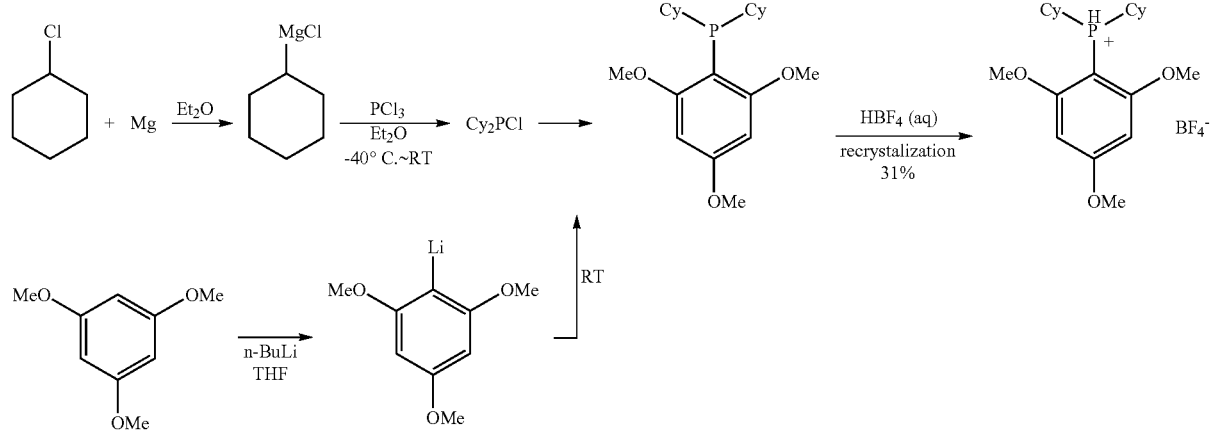

To a solution of trimethoxybenzene (2.0182 g, 12 mmol, 12 mmol) in 50 mL of dry THF was added n-butyl lithium (0.8 mL, 2.5 M in hexane, 12 mmol) dropwise under $N_2$. The mixture was stirred for 11.5 hours at room temperature, at which time the reaction system was then cooled to −78° C. Chlorodicyclohexyl phosphine was added dropwise. After the mixture is stirred for 30 minutes, the temperature is warmed to room temperature and the reaction was stirred for another 18 hours.

To another dried three-neck flask was added $PCl_3$ (0.92 mL, d=1.50 g/mL, 1.38 g, 10 mmol) and 50 mL of dry $Et_2O$. The solution was cooled to −40° C. and cyclohexylmagnesium chloride (25 mL, 0.80 M, 20 mmol) was added dropwise at this temperature within 10 min. After the addition, the resulting mixture was allowed to stir at 30° C. for 7.4 h. The above prepared S-trimethoxyphenyl lithium solution was then added in one portion. After another 11.5 h with stirring at 30° C., the reaction was quenched with 40 mL of aqueous $HBF_4$ (38% wt) with vigorous stirring for 20 min. Water (100 mL) was added and the resulting mixture was extracted with $CH_2Cl_2$ (100+50 mL), washed with 50 mL of brine, and dried over anhydrous $Na_2SO_4$. Filtration, evaporation and recrystallization by $Et_2O/CH_2Cl_2$ afforded 1.4092 g of dicyclohexyl (2,4,6-trimethoxyphenyl)phosphine tetrafluoroborate is obtained and the yield is 31%.

m.p.: 142.6-143.4° C.; $^1$H NMR (300 MHz, $CDCl_3$) δ 6.55 (dt, $J_1$=480 Hz, $J_2$=6.9 Hz, 1H), 6.23 (d, J=4.2 Hz, 2H), 3.90 (s, 9H), 2.80-2.58 (m, 2H), 2.12-1.97 (m, 2H), 1.90-1.60 (m, 8H), 1.51-1.09 (m, 10H); $^{13}$C NMR (75 MHz, $CDCl_3$) δ 168.4, 164.2, 91.5 (d, J=6.4 Hz), 78.9 (d, J=88.3 Hz), 56.5, 56.1, 29.0 (d, J=45.8 Hz), 27.9 (d, J=2.1 Hz), 26.7 (d, J=3.2 Hz), 25.8 (d, J=14.2 Hz), 25.6 (d, J=13.0 Hz), 24.9; $^{31}$P NMR (121 MHz, $CDCl_3$) δ 7.09; IR (KBr) v ($cm^{-1}$) 3417, 2933, 2854, 1599, 1577, 1468, 1452, 1416, 1344, 1233, 1210, 1164, 1130, 1108, 1084; MS (70 eV, EI) m/z (%): 364 ($M^+$-$HBF_4$, 26.75), 349 ($M^+$-$HBF_4$-Me, 7.41), 333 ($M^+$-$HBF_4$—OMe, 31.52), 309 ($M^+$-$BF_4$—$C_4H_8$, 19.82), 282 ($M^+$-$BF_4$-Cy, 100), 199 ($M^+$-$BF_4$-2Cy, 78.01); (computed value: Anal. Calcd. For) $C_{21}H_{34}BF_4O_3P$, C, 55.77; H, 7.58. value measured. Found: C, 55.83; H, 7.54.

Example 3

Synthesis of dicyclohexyl(2,6-dimethoxyphenyl)phosphine tetrafluoroborate

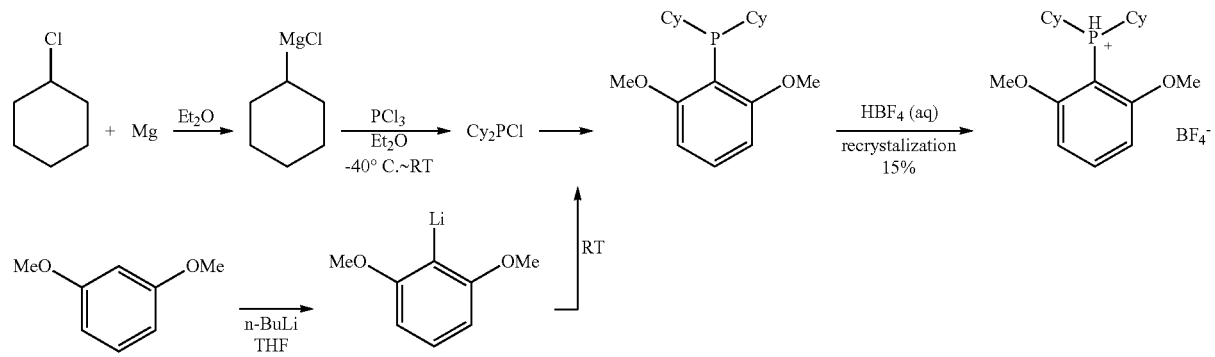

The synthesis is carried in the same manner as the method described in example 2. The difference is that: the starting material is trichlorophosphine (0.92 mL, 1.38 g, 10 mmol), cyclohexylmagnesium chloride (0.8 M in $Et_2O$), 1,3-Dimethoxybenzene (1.60 mL, 1.68 g, 12 mmol) and n-butyl lithium (2.5 M in hexane). After the reaction is done in ether/ tetrahydrofuran, tetrafluoborate aqueous solution is used to quench the reaction, and dialkyl(2,6-methoxyphenyl)phosphine tetrafluoroborate is obtained. The yield is 15%.

$^1$H NMR (300 MHz, CDCl$_3$) δ 7.63-7.71 (m, 1H), 6.80-6.65 (m, 2H), 6.77 (dt, J$_1$=486 Hz, J$_2$=6.3 Hz, 1H); 3.95 (s, 6H), 2.90-2.70 (m, 2H), 2.20-2.06 (m, 2H), 1.95-1.63 (m, 8H), 1.56-1.10 (m, 10H); $^{31}$P NMR (121 MHz, CDCl$_3$) δ 7.36.

Example 4

Synthesis of 4-Methoxybiphenyl

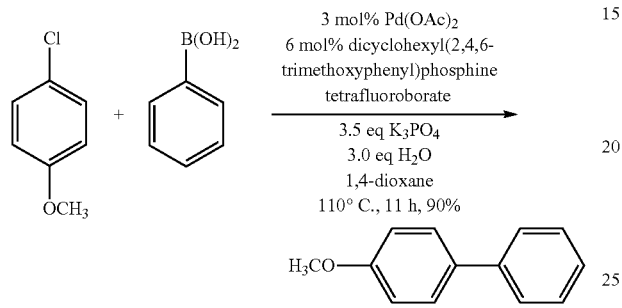

To a rubber-capped Schlenk vessel was added K$_3$PO$_4$ (298.4 mg, 1.4 mmol). This equipment was dried with flame under vacuum and backfilled with nitrogen for three times. Then Pd(OAc) (2.7 mg, 0.012 mmol), dicyclohexyl(2,4,6-trimethoxyphenyl)phosphine tetrafluoroborate (11.0 mg, 0.024 mmol), phenyl bronic acid (99.8 mg, 98%, 0.80 mmol), and 0.5 mL of dioxane were added sequentially to the Schlenk vessel. After being stirred for about 5 min at room temperature, p-methoxyphenyl chloride (56.5 mg, 0.40 mmol), another 0.5 mL of dioxane, and 21.5 μL of water (21.5 mg, 1.2 mmol) were added sequentially in one portion. The resulting mixture was heated at 110° C. with a preheated oil bath. After 11 h, the reaction was complete as monitored by GC. The reaction mixture was then cooled and diluted by 10 mL of CH$_2$Cl$_2$ and filtered through a short column of silica gel (eluent: 2×10 mL of CH$_2$Cl$_2$). Evaporation and purification by chromatography (petroleum ether/ether=60/1) on silica gel afforded 4-Methoxybiphenyl (65.9 mg, 90%)

m.p.: 87.2-87.8° C.; $^1$H NMR (300 MHz, CDCl$_3$) δ 7.65-7.55 (m, 4H), 7.52-7.41 (m, 2H), 7.40-7.32 (m, 1H), 7.08-7.00 (m, 2H), 3.89 (s, 3H); $^{13}$C NMR (75 MHz, CDCl$_3$) δ 159.1, 140.7, 133.7, 128.7, 128.1, 126.7, 126.6, 114.1, 55.3; IR (KBr) ν (cm$^{-1}$) 3069, 3027, 3003, 2955, 2895, 2829, 1606, 1522, 1488, 1464, 1288, 1270, 1251, 1201, 1184, 1035; MS (70 eV, EI) m/z (%): 185 (M$^+$+1, 14.24), 184 (M$^+$, 100).

Example 5

Synthesis of (R)-(−)-3-propyl-4,5-diphenyl-2(5H)-furanone

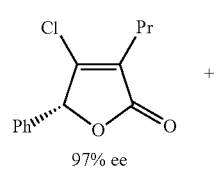

97% ee

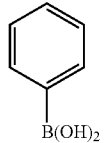

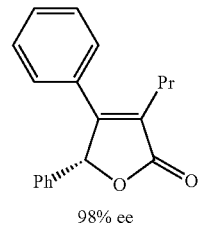

98% ee

Under the protection of nitrogen, phenylboronic acid (19.1 mg, 98%, 0.15 mmol), palladium acetate (1.2 mg, 0.0054 mmol), dicyclohexyl(2,4,6-trimethoxyphenyl)phosphine tetrafluoroborate (11.0 mg, 0.024 mmol), potassium carbonate (63.1 mg, 0.46 mmol) and 0.5 mL of anhydrous toluene are added sequentially to the reactor. The mixture is stirred at room temperature for 3 min and then (R)-(−)-3-propyl-4-chloride-5-phenyl-2(5H)-furanone (22.8 mg, 0.096 mmol, 97% ee) and 0.5 mL of anhydrous toluene are added into the reactor. The reaction is carried out at 110° C. for 6 min and quenched with 10 mL of water. Extracted with ether, wash with brine, dried over anhydrous sodium sulfate, and purified by column chromatography afforded 20.1 mg of (R)-(−)-3-propyl-4,5-diphenyl-2(5H)-furanone. The yield is 75%, 98% ee.

HPLC condition: Chiralpak OD-H, rate: 0.8 mL/min, λ=230 nm, n-hexane/1-PrOH=65/35. m.p.: 103.8-104.9° C. (n-hexane). $^1$H NMR (300 MHz, CDCl$_3$) δ 7.37-7.15 (m, 10H), 6.16-6.14 (m, 1H), 2.58-2.42 (m, 2H), 1.78-1.60 (m, 2H), 0.98 (t, J=7.4 Hz, 3H); $^{13}$C NMR (75 MHz, CDCl$_3$) δ 174.1, 159.1, 134.9, 131.5, 129.5, 129.1, 128.7, 128.5, 127.8, 127.3, 83.7, 26.3, 21.5, 14.1; IR (KBr) ν (cm$^{-1}$) 3057, 3027, 2958, 2939, 2870, 1749, 1734, 1649, 1498, 1455, 1445, 1355, 1340, 1206, 1126, 1090, 1072, 1014; MS (70 eV, EI) m/z (%): 279 (M$^+$+1, 16.57), 278 (M$^+$, 77.10), 173 (100); Anal. Calcd. for C$_{19}$H$_{18}$O$_2$: C, 81.99; H, 6.52. Found: C, 82.00; H, 6.53. $[α]^{20}_D$=−152.0.

Example 6

(Control example) Coupling reaction of optically active 4-chloride cicrotoic acid lactone with Cy$_3$P.HBF$_4$ being the ligand

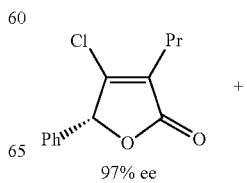

97% ee

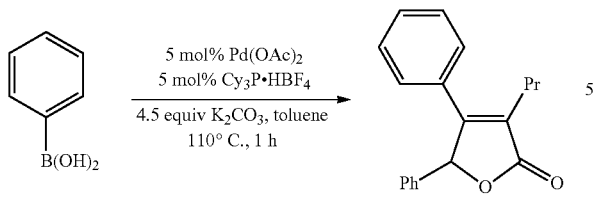

This reaction is carried out in the same manner as the reaction in example 5. The difference is that, the reactans are (R)-(−)-3-propyl-4-chloride-5-phenyl-2(5H)— furanone (23.9 mg, 0.10 mmol, 97% ee), phenylboronic acid (19.2 mg, 98%, 0.15 mmol), palladium acetate (1.1 mg, 0.005 mmol), tricyclohexylphosphonium tetrafluoroborate (1.8 mg, 0.005 mmol), potassium carbonate (62.0 mg, 0.45 mmol) and 1 mL of anhydrous toluene. The reactants are reacted for 1 hours under 110° C., and 3-methyl-4,5-diphenyl-2(5H)-furanone is obtained. The yield is 67%, 0% ee, 9% the starting material is recycled.

Example 7

(Control example) Coupling reaction of optically active 4-chloride cicrotoic acid lactone using 2-dicyclohexylphosphino-2',6'-dimethoxybiphenyl as the catalyst

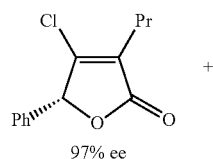

97% ee

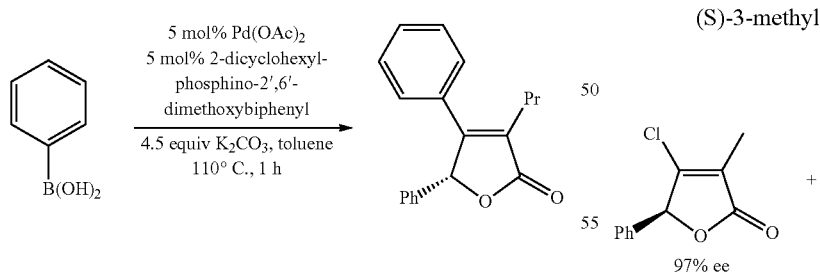

This reaction is carried out in the same manner as the reaction in example 5. The difference is that, the reactans are (R)-(−)-3-propyl-4-chloride-5-phenyl-2(5H)— furanone (22.9 mg, 0.097 mmol, 97% ee), phenylboronic acid (19.0 mg, 98%, 0.15 mmol), palladium acetate (1.1 mg, 0.005 mmol), 2-dicyclohexylphosphino-2',6'-dimethoxybiphenyl (2.1 mg, 0.005 mmol), potassium carbonate (62.1 mg, 0.45 mmol) and 1 mL of anhydrous toluene. The reactants are reacted for 1 hours under 110° C., and 3-methyl-4,5-diphenyl-2(5H)-furanone is obtained. The yield is 40%, <16% ee, 11% the starting material is recycled.

Example 8

Synthesis of (R)-(−)-3-propyl-4,5-diphenyl-2(5H)-furanone

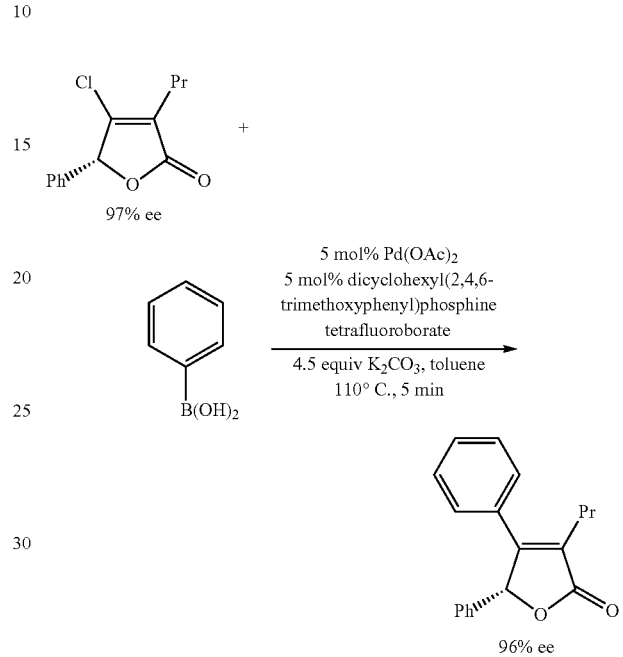

96% ee

This reaction is carried out in the same manner as the reaction in example 5. The difference is that 5% dicyclohexyl (2,4,6-trimethoxyphenyl)phosphine is used as the ligand to react for 5 minutes. 70% yield is achieved. 96% ee (R)-(−)-3-propyl-4,5-diphenyl-2(5H)-furanone is obtained.

Example 9

Synthesis of (S)-3-methyl-4,5-diphenyl-2(5H)-furanone

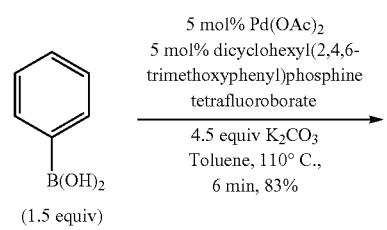

-continued

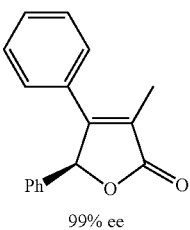

99% ee

This reaction is carried out in the same manner as the reaction in example 5. The difference is that, the reactans are (S)-3-methyl-4-chloride-5-phenyl-2(5H)— furanone (20.2 mg, 0.097 mmol), phenylboronic acid (19.0 mg, 98%, 0.15 mmol), palladium acetate (1.1 mg, 0.01 mmol), dicyclohexyl (2,4,6-trimethoxyphenyl)phosphine tetrafluoroborate (2.5 mg, 0.0055 mmol), potassium carbonate (62.3 mg, 0.45 mmol) are reacted in 2 mL of anhydrous toluene at 110° C. for 6 minutes and 20.1 mg (S)-3-methyl-4,5-diphenyl-2(5H)-furanone is obtained. The yield is 83%, 99% ee.

$[\alpha]^{20}_D$+179.5 (c=0.96, CHCl$_3$); liquid; $^1$H NMR (300 MHz, CDCl$_3$) δ 7.40-7.17 (m, 10H), 6.21-6.16 (m, 1H), 2.16 (d, J=1.8 Hz, 3H); $^{13}$C NMR (75 MHz, CDCl$_3$) δ 174.5, 158.3, 135.0, 131.4, 129.6, 129.2, 128.79, 128.77, 128.0, 127.5, 124.1, 83.7, 10.3.

Example 10

Synthesis of (S)-(+)-3-methyl-4-(methoxyphenyl)-5-phenyl-2(5H)-furanone

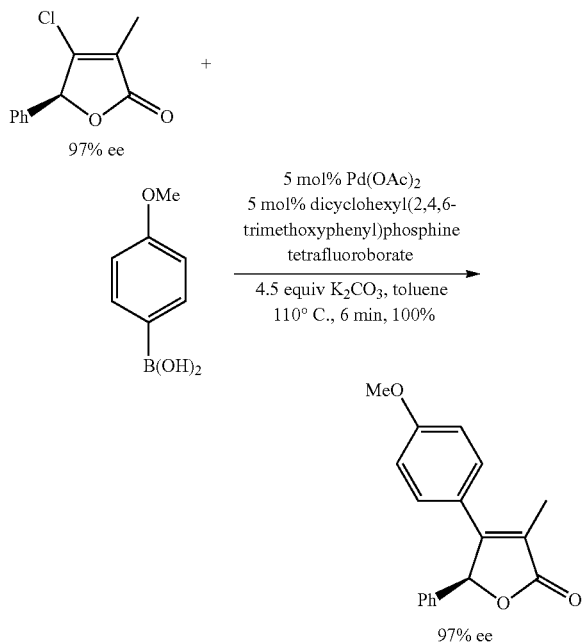

This reaction is carried out in the same manner as the reaction in example 5. The difference is that (S)-(+)-3-methyl-4-chloride-5-phenyl-2(5H)— furanone (42.1 mg, 0.20 mmol, 97% ee), methoxyphenylboronic acid (47.3 mg, 97%, 0.30 mmol), palladium acetate (2.2 mg, 0.0098 mmol), dicyclohexyl(2,4,6-trimethoxyphenyl)phosphine tetrafluoroborate (4.6 mg, 0.010 mmol), potassium carbonate (123.4 mg, 0.89 mmol) are reacted in 2 mL of anhydrous toluene at 110° C. for 6 minutes and 56.5 mg of (S)-3-methyl-4-(methoxyphenyl)-5-phenyl-2(5H)-furanone is obtained. The yield is 100%, 97% ee.

$[\alpha]^{20}_D$=+ 229.7 (c=1.05, CHCl$_3$); liquid; $^1$H NMR (300 MHz, CDCl$_3$) δ 7.32-7.19 (m, 7H), 6.90-6.83 (m, 2H), 6.18-6.13 (m, 1H), 3.78 (s, 3H), 2.18 (d, J=1.5 Hz, 3H); $^{13}$C NMR (75 MHz, CDCl$_3$) δ 174.7, 160.4, 157.6, 135.4, 129.6, 129.1, 128.7, 127.5, 123.6, 122.1, 114.1, 83.4, 55.2, 10.5; IR (neat) v (cm$^{-1}$) 3063, 3033, 3003, 2934, 2840, 1747, 1651, 1607, 1572, 1515, 1456, 1421, 1383, 1343, 1295, 1256, 1182, 1095, 1035; MS (70 eV, EI) m/z (%): 281 (M$^+$+1, 15.43), 280 (M$^+$, 78.42), 175 (100); HRMS calcd for C$_{18}$H$_{16}$O$_3$ (M$^+$): 280.1099. Found: 280.1097.

Example 11

Synthesis of (R)-(−)-3-methyl-5-pentyl-4(methoxyphenyl)-2(5H)-furanone

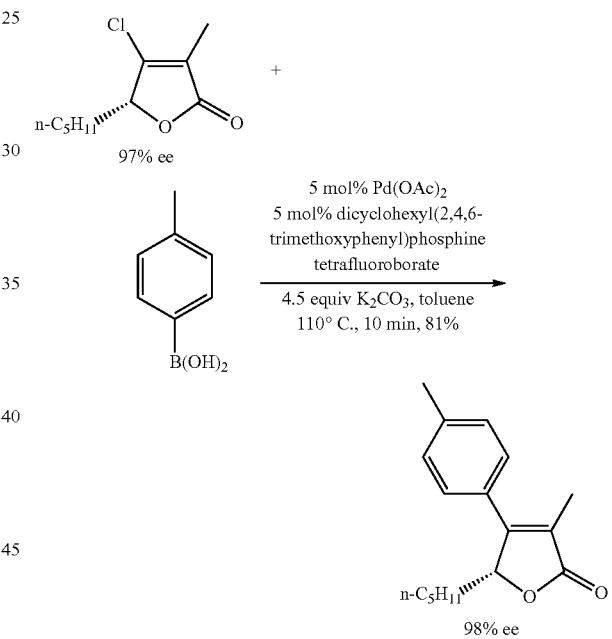

This reaction is carried out in the same manner as the reaction in example 5. The difference is that (S)-(−)-3-methyl-5-pentyl-4-chloride-2(5H)— furanone (19.7 mg, 0.097 mmol, 97% ee) and 2.0 equivalent methoxyphenyl boronic acid are used as starting material. Under standard conditions, the yield can reach 81%, ee value is 98%, and corresponding (R)-(−)-3-methyl-5-pentyl-4(methoxyphenyl)-2(5H)-furanone is obtained.

$[\alpha]^{20}_D$=−268.2 (c=1.00, CHCl$_3$); $^1$H NMR (300 MHz, CDCl$_3$) δ 7.31-7.21 (m, 4H), 5.36-5.29 (m, 1H), 2.42 (s, 3H), 2.04 (d, J=1.8 Hz, 3H), 1.85-1.75 (m, 1H), 1.49-1.31 (m, 3H), 1.31-1.10 (m, 4H), 0.83 (t, J=6.8 Hz, 3H); $^{13}$C NMR (75 MHz, CDCl$_3$) δ 174.8, 159.5, 140.0, 129.7, 128.7, 127.6, 122.8, 81.7, 33.0, 31.3, 24.1, 22.4, 21.4, 13.9, 10.0; IR (neat) v (cm$^{-1}$) 2955, 2927, 2860, 1752, 1656, 1614, 1515, 1454, 1383, 1337, 1228, 1090, 1056; MS (70 eV, EI) m/z (%): 259

(M++1, 2.67), 258 (M+, 13.76), 159 (100); HRMS calcd for C$_{17}$H$_{22}$O$_2$ (M+): 258.1620. Found: 258.1620.

Example 12

Synthesis of (S)-3-methyl-5-phenyl-4-(methoxyphenyl)-2(5H) furanone

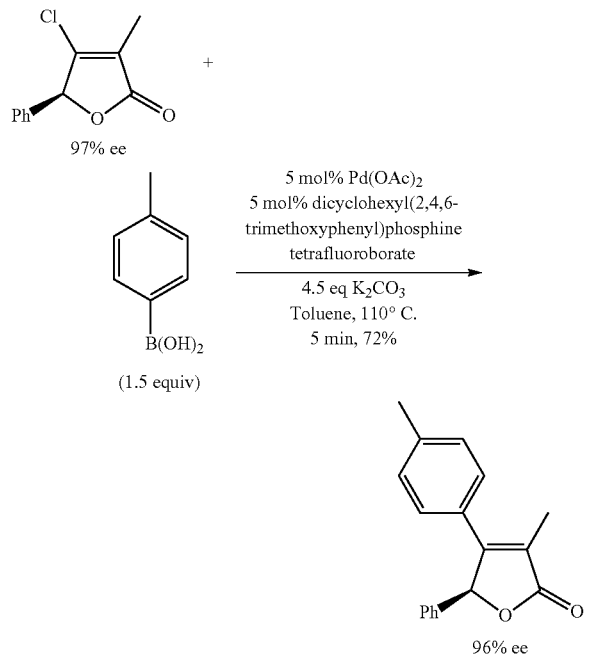

This reaction is carried out in the same manner as the reaction in example 5. The difference is that (S)-(+)-3-methyl-5-4-chloride-5-phenyl-2(5H)— furanone (20.1 mg, 0.096 mmol, 97% ee), methoxyphenyl boronic acid (20.4 mg, 98%, 0.15 mmol), palladium acetate (1.2 mg, 0.0054 mmol), dicyclohexyl(2,4,6-trimethoxyphenyl)phosphine tetrafluoroborate (2.2 mg, 0.0049 mmol), potassium carbonate (62.8 mg, 0.46 mmol) are reacted in 1 mL of toluene at 110° C. for 5 minutes and 18.3 mg of (S)-3-methyl-4-(methoxyphenyl)-5-phenyl-2(5H)-furanone is obtained. The yield is 100%, 96% ee.

[α]$^{20}_D$=+ 191.3 (c=0.83, CHCl$_3$); liquid; $^1$H NMR (300 MHz, CDCl$_3$) δ 7.31-7.12 (m, 9H), 6.20-6.16 (m, 1H), 2.32 (s, 3H), 2.16 (d, J=1.5 Hz, 3H); $^{13}$C NMR (75 MHz, CDCl$_3$) δ 174.7, 158.2, 140.0, 135.3, 129.5, 129.1, 128.8, 128.5, 127.9, 127.5, 123.3, 83.6, 21.3, 10.4.

Example 13

Synthesis of 3-methyl-4-(methoxyphenyl)-5-phenyl-2(5H)-furanone

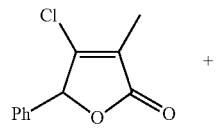

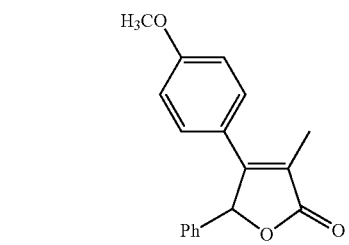

This reaction is carried out in the same manner as the reaction in example 4. The difference is that 3-methyl-4-chloride-5-phenyl-2(5H)— furanone (42.0 mg, 0.2 mmol), methoxyphenyl boronic acid (46.5 mg, 97%, 0.3 mmol), palladium acetate (2.3 mg, 0.01 mmol), dicyclohexyl(2,4,6-trimethoxyphenyl)phosphine (7.3 mg, 0.02 mmol), potassium carbonate (82.3 mg, 0.6 mmol) are reacted in 1 mL of toluene at 110° C. for 35 minutes and 3-methyl-4-(methoxyphenyl)-5-phenyl-2(5H)— furanone is obtained. The yield is 100%.

Example 14

Synthesis of 2,6-dimethyl-3',5'-dimethoxydiphenyl

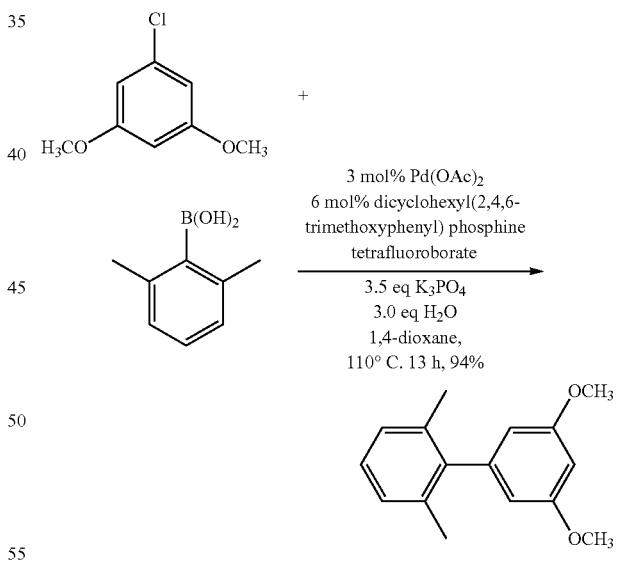

This reaction is carried out in the same manner as the reaction in example 4. The difference is that reactants are 3,5-dimethoxychlorobenzene (169.9 mg, 0.98 mmol), 2,6-dimethoxyphenyl boronic acid (332.0 mg, purity: 90%, 2.0 mmol), palladium acetate (27. mg, 0.030 mmol), dicyclohexyl(2,4,6-trimethoxyphenyl)phosphine tetrafluoborate (27.3 mg, 0.060 mmol), potassium phosphate (742.5 mg, 3.5 mmol), water (54.0 pt, 3.0 mmol) and 2.5 mL of 1,4-dioxane are reacted at 110° C. for 11 hours and 223.5 mg of 2,6-dimethyl-3',5'-dimethoxydiphenyl is obtained. The yield is 94%.

$^1$H NMR (300 MHz, CDCl$_3$) δ 7.18-7.02 (m, 3H), 6.45 (t, J=2.2 Hz, 1H), 6.31 (d, J=2.4 Hz, 2H), 3.76 (s, 6H), 2.08 (s, 6H); $^{13}$C NMR (75 MHz, CDCl$_3$) δ 160.8, 143.0, 141.7, 135.8, 127.1, 127.0, 106.8, 98.5, 55.1, 20.5; IR (neat) v (cm$^{-1}$) 3057, 2999, 2955, 2835, 1592, 1455, 1421, 1377, 1344, 1327, 1296, 1250, 1205, 1154, 1064, 1033; MS (70 eV, EI) m/z (%): 243 (M$^+$+1, 18.52), 242 (M$^+$, 100).

Example 15

Synthesis of 2,6-dimethyl-3'-methoxy diphenyl

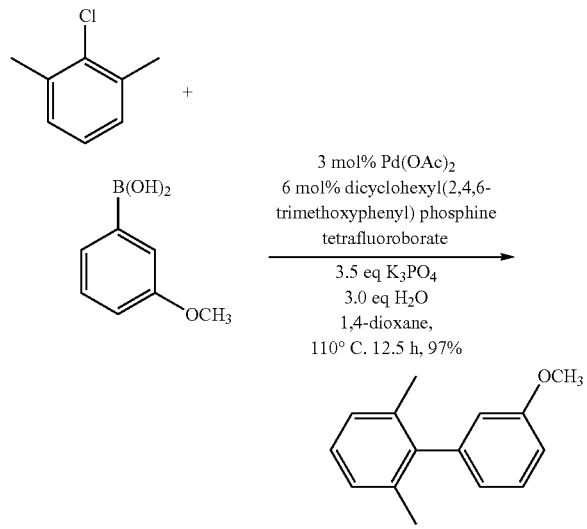

This reaction is carried out in the same manner as the reaction in example 4. The difference is that reactants are 2,6-dimethoxychlorobenzene (139.1 mg, 0.99 mmol), 3-methoxyphenyl boronic acid (313.8 mg, 97%, 2.0 mmol), palladium acetate (6.5 mg, 0.029 mmol), dicyclohexyl(2,4,6-trimethoxyphenyl)phosphine tetrafluoborate (27.1 mg, 0.060 mmol), potassium phosphate (742.6 mg, 3.5 mmol), water (54.0 μL, 3.0 mmol) and 2.5 mL of 1,4-dioxane are reacted at 110° C. for 11 hours and 202.8 mg of 2,6-dimethyl-3"-methoxydiphenyl is obtained. The yield is 97%.
$^1$H NMR (300 MHz, CDCl$_3$) δ 7.34-7.26 (m, 1H), 7.17-7.05 (m, 3H), 6.88-6.83 (m, 1H), 6.75-6.67 (m, 2H), 3.77 (s, 3H), 2.04 (s, 6H); $^{13}$C NMR (75 MHz, CDCl$_3$) δ 159.6, 142.4, 141.6, 135.9, 129.4, 127.2, 127.0, 121.3, 114.4, 112.0, 55.0, 20.7; IR (neat) v (cm$^{-1}$) 3063, 2999, 2954, 2833, 1608, 1578, 1466, 1430, 1377, 1309, 1288, 1247, 1208, 1177, 1050, 1026; MS (70 eV, EI) m/z (%): 213 (M$^+$+1, 17.22), 212 (M$^+$, 100).

Example 16

Synthesis of 4-methoxydiphenyl

This reaction is carried out in the same manner as the reaction in example 4. The difference is that 0.06 equivalent of dicyclohexyl(2,6-dimethoxyphenyl)phosphine tetrafluoborate is used as catalyst. The reaction is carried out for 12 hours and 4-methoxydiphenyl is obtained. The yield is 41%.

Example 17

Synthesis of 4-methoxydiphenyl

This reaction is carried out in the same manner as the reaction in example 4. The difference is that 0.06 equivalent of dicyclohexyl(2,6-diisopropoxyphenyl)phosphine tetrafluoborate is used as catalyst. The reaction is carried out for 12 hours and 4-methoxydiphenyl is obtained. The yield is 100%.

Example 18

Synthesis of 4-methoxydiphenyl

This reaction is carried out in the same manner as the reaction in example 4. The difference is that 3 equivalent of potassium carbonate is used as base. Toluene is the solvent. The reaction is carried out at 110° for 28 hours and 4-methoxydiphenyl is obtained. The yield is 41%.

Example 19

Synthesis of 4-methoxydiphenyl

This reaction is carried out in the same manner as the reaction in example 4. The difference is that 3 equivalent of potassium carbonate is used as base. The reaction is carried out at 110° for 28 hours and 4-methoxydiphenyl is obtained. The yield is 88%.

Example 20

Synthesis of 4-methoxydiphenyl

This reaction is carried out in the same manner as the reaction in example 4. The difference is that 3 equivalent of cesium fluoride is used as base. The reaction is carried out at 110° for 24 hours and 4-methoxydiphenyl is obtained. The yield is 80%.

Example 21

Synthesis of 4-methoxydiphenyl

This reaction is carried out in the same manner as the reaction in example 4. The difference is that 3 equivalent of cesium carbonate is used as base. The reaction is carried out at 110° for 13 hours and 4-methoxydiphenyl is obtained. The yield is 88%.

Example 22

Synthesis of N-phenyl-N-methyl-3,5-dimethylphenylamine

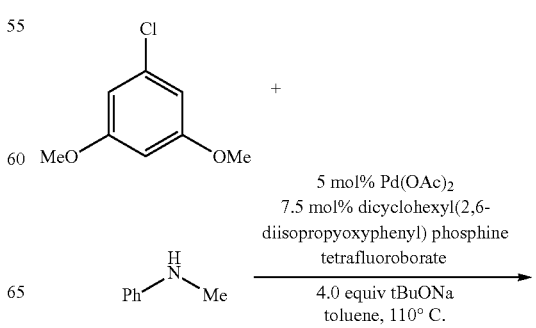

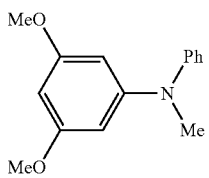

Under the protection of nitrogen, palladium acetate (4.4 mg, 0.02 mmol), dicyclohexyl(2,6-dimethoxyphenyl)phosphine tetrafluoroborate (14.4 mg, 0.03 mmol), sodium tert-butoxide (155.1 mg, 97%, 1.6 mmol), 3,5-dimethoxychlorobenzene (68.8 mg, 0.4 mmol) and 1 mL of toluene were added to the reactor sequentially. The mixture is stirred at room temperature for 4 minutes. N-methylphenyl amine (86.1 mg, 0.8 mmol) and another 1 mL of toluene were added into the reactor. The reactor was heated to 110° C. and the temperature is maintained for 24 hours. After the reactor is cooled, 10 mL of methylene dichloride was used to quench the reaction. Filtration and column chromatography (petroleum: ethyl acetate: triethylamine=100:1:1) afforded 74.5 mg of N-phenyl-N-methyl-3,5-dimethylphenylamine. The yield is 77%.

$^1$H NMR (300 MHz, CDCl$_3$) δ 7.38-7.29 (m, 2H), 7.16-7.10 (m, 2H), 7.09-7.01 (m, 1H), 6.16 (d, J=2.1 Hz, 2H), 6.10 (t, J=2.0 Hz, 1H), 3.76 (s, 6H), 3.32 (s, 3H); $^{13}$C NMR (75 MHz, CDCl$_3$) δ 161.3, 150.8, 148.6, 129.2, 122.4, 122.3, 97.4, 92.4, 55.2, 40.3.

Example 23

Synthesis of N-phenyl-N-methyl-3,5-dimethylphenylamine

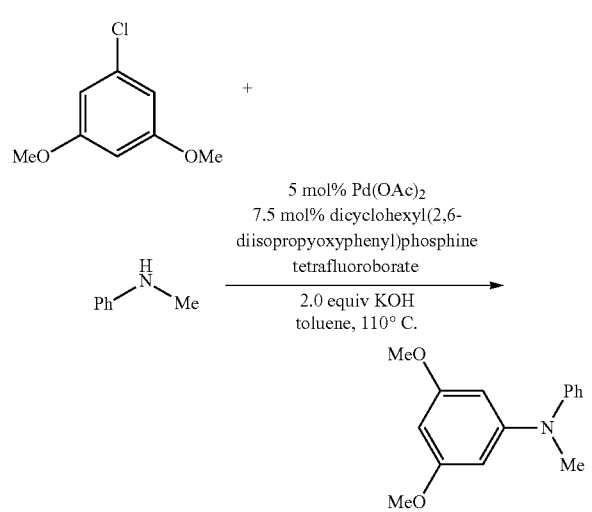

Under the protection of nitrogen, 0.05 equivalent of palladium acetate, 0.075 equivalent of dicyclohexyl(2,6-diisopropoxyphenyl)phosphine tetrafluoborate, 2.0 equivalent of potassium hydroxide, 1.0 equivalent of 3,5-dimethoxychlorobenzene and 1.2 equivalent of phenylamine were reacted in toluene at 110° C. for 3 hours. N-phenyl-N-methyl-3,5-dimethylphenylamine was obtained with a yield of 93%.

Example 24

Synthesis of N-phenyl-N-methyl-3,5-dimethylphenylamine

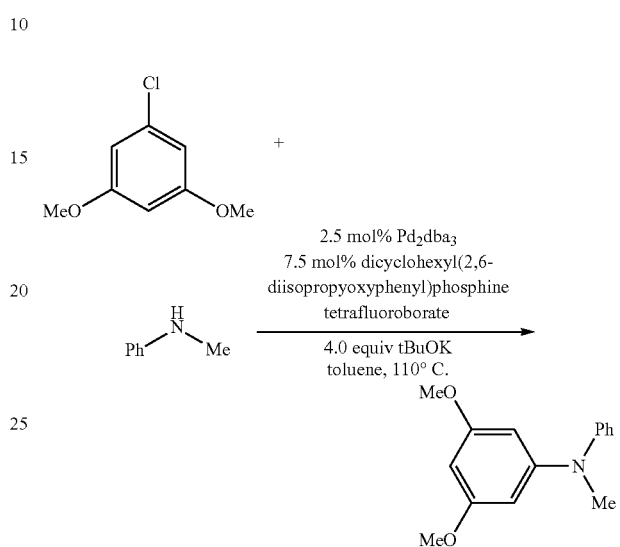

Under the protection of nitrogen, 0.025 equivalent of tris(dibenzylideneacetone)dipalladium (Pd$_2$(dba)$_3$CHCl$_3$), 0.075 equivalent of dicyclohexyl(2,6-diisopropoxyphenyl)phosphine tetrafluoborate, 4.0 equivalent of potassium tert-butoxide, 1.0 equivalent of 3,5-dimethoxychlorobenzene and 2.0 equivalent of phenylamine were reacted in toluene at 110° C. for 24 hours. N-phenyl-N-methyl-3,5-dimethylphenylamine was obtained with a yield of 57%.

Example 25

Synthesis of N-phenyl-N-methyl-3,5-dimethylphenylamine

The reaction was carried out in the same manner as the reaction in example 22. The difference was that 4.0 equivalent of sodium hydride was used as base. After the reaction was carried out at 110° C. for 24 hours, N-phenyl-N-methyl-3,5-dimethylphenylamine was obtained with a yield of 56%.

We claim:

1. A method for synthesizing a biphenyl compound, comprising reacting an arylchloride and an arylboronic acid in presence of a dialkyl(2,4,6- or 2,6-alkoxyphenyl)phosphine or its tetrafluoroborate, a palladium catalyst, a base, and water to obtain a biphenyl coupling compound via Suzuki coupling reaction, wherein the arylchloride has an inert carbon-chlorine bond that selectively undergoes coupling reaction with the arylboronic acid, and the dialkyl(2,4,6- or 2,6-alkoxyphenyl)phosphine or its tetrafluoroborate has a structure of

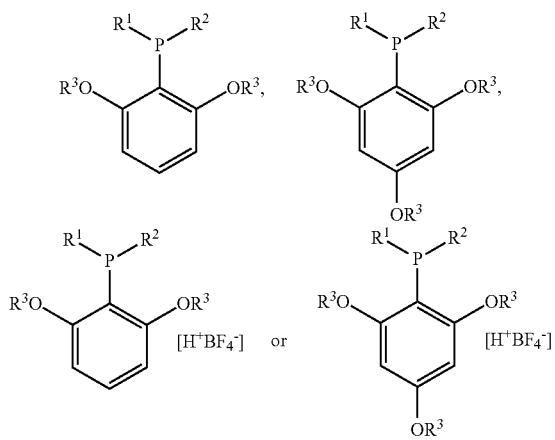

wherein R¹ and R² is cyclopropyl, cyclopentyl, cyclohexyl, or admantyl group, respectively; and R³ is an alkyl group.

2. The method for synthesizing a biphenyl compound as described in claim 1, wherein the Suzuki coupling reaction is conducted under protection of an inert gas, at 80-120° C., in an organic solvent to obtain the biphenyl coupling compound.

3. A method for synthesizing an aryl-substituted lactone compound, comprising
reacting a chloride and an arylboronic acid in presence of a dialkyl(2,4,6- or 2,6-alkoxyphenyl)phosphine or its tetrafluoroborate, a palladium catalyst, a base, and water to obtain an aryl-substituted lactone compound,
wherein the dialkyl(2,4,6- or 2,6-alkoxyphenyl)phosphine or its tetrafluoroborate has a structure of

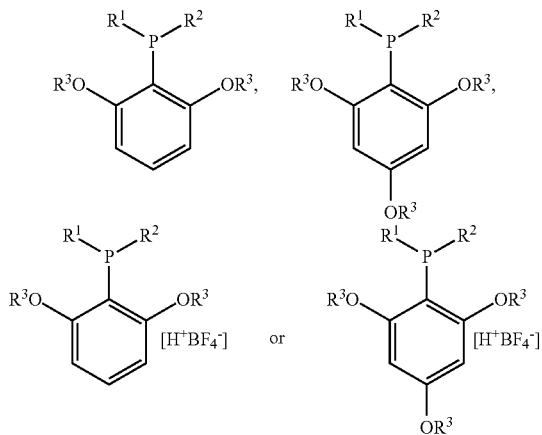

wherein R¹ and R² is cyclopropyl, cyclopentyl, cyclohexyl, or admantyl group, respectively; and R³ is an alkyl group, and
wherein the palladium catalyst is palladium acetate,
the base is potassium carbonate,
the organic solvent is toluene,
the chloride has an inert carbon-chlorine bond that selectively undergoes coupling reaction with the arylboronic acid, and is an optically active chlorolactone having a structure of

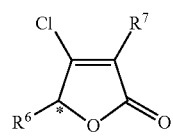

R⁶ being an alkyl, aryl, or heterocyclic group; R⁷ being an alkyl group; the heterocyclic group is thiophene, furan, or pyridine; * being an optically active carbon,
molar ratio of the palladium acetate, the dialkyl(2,4,6- or 2,6-alkoxyphenyl)phosphine or its tetrafluoroborate, the potassium carbonate, the arylboronic acid, and the optically active chlorolactone is 0.05:(0.05~0.10):(3.0~4.5):(1.2~2.0):1.0, and the aryl-substituted lactone compound substantially preserves the optical activity of the chlorolactone.

4. The method for synthesizing an aryl-substituted lactone compound as described in claim 3, wherein the optically active lactone compound has maintained its configuration and optical purity, and is represented by a formula

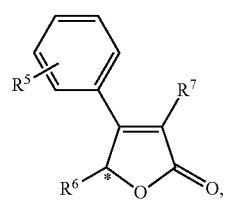

wherein R⁵ is an ortho-, meta-, or para-substituted alkyl, alkoxy, aryl, or hydrogen; R⁶ is an alkyl, phenyl, or heterocyclic group; R⁷ is an alkyl group; * is an optically active carbon; said heterocyclic group is thiophene, furan, or pyridine.

5. The method for synthesizing a biphenyl compound as described in claim 2, wherein the organic solvent is 1,4-dioxane or toluene.

6. The method for synthesizing a biphenyl compound as described in claim 1, wherein a molar ratio of the base, the palladium catalyst, the dialkyl(2,4,6- or 2,6-alkoxyphenyl)phosphine or its tetrafluoroborate, the arylboronic acid, water, and the chloride is (2.0-4.0):(0.03~0.05):(0.06~0.10):(1.5~2.5):(0~5.0):1.0.

7. The method for synthesizing a biphenyl compound as described in claim 1, wherein the base is potassium carbonate, potassium phosphate, cesium carbonate, or cesium fluoride.

8. The method for synthesizing a biphenyl compound as described in claim 1, wherein the chloride is an arylchloride having a structure of

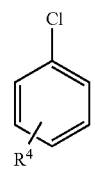

R⁴ is an ortho-, meta-, or para-substituted alkyl, alkoxy, or hydrogen.

9. The method for synthesizing a biphenyl compound as described in claim 1, wherein the arylboronic acid has a structure of $R^5C_6H_4B(OH)_2$, and $R^5$ is an ortho-, meta-, or para-substituted alkyl, alkoxy, aryl, or hydrogen.

10. A method for synthesizing an aromatic secondary or tertiary amine, comprising reacting an arylchloride and an organic amine in presence of a dialkyl(2,4,6- or 2,6-alkoxyphenyl)phosphine or its tetrafluoroborate, a palladium catalyst, and a base, to obtain a secondary or tertiary aromatic amine via a carbon-nitrogen bond formation reaction, wherein the arylchloride has an inert carbon-chlorine bond that selectively undergoes the carbon-nitrogen bond formation reaction with the organic amine, and the dialkyl(2,4,6- or 2,6-alkoxyphenyl)phosphine or its tetrafluoroborate has a structure of

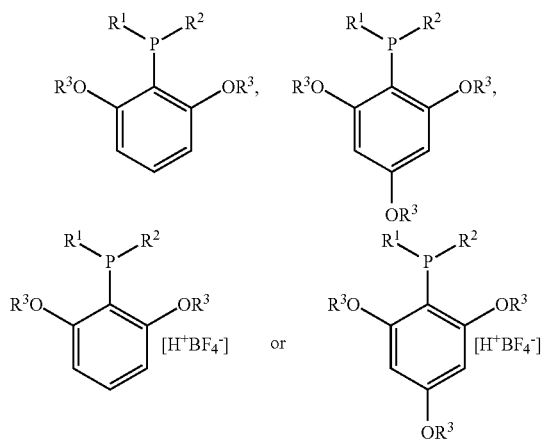

wherein $R^1$ and $R^2$ is cyclopropyl, cyclopentyl, cyclohexyl, or admantyl group, respectively; and $R^3$ is an alkyl group.

11. The method for synthesizing an aromatic secondary or tertiary amine as described in claim 10, wherein the carbon-nitrogen bond formation reaction is conducted under protection of an inert gas in an organic solvent.

12. The method for synthesizing an aromatic secondary or tertiary amine as described in claim 10, wherein molar ratio of the base, the palladium catalyst, the dialkyl(2,4,6- or 2,6-alkoxyphenyl)phosphine or its tetrafluoroborate, the organic amine, and the arylchloride is (1.5-4.0):(0.01~0.05):(0.015~0.10):(1.2~2.5):1.0.

13. The method for synthesizing an aromatic secondary or tertiary amine as described in claim 11, wherein the organic solvent is 1,4-dioxane or toluene.

14. The method for synthesizing an aromatic secondary or tertiary amine as described in claim 10, wherein the palladium catalyst is palladium acetate or tris(dibenzylideneacetone)dipalladium.

15. The method for synthesizing an aromatic secondary or tertiary amine as described in claim 10, wherein the base is potassium tert-butoxide, sodium tert-butoxide, potassium phosphate, potassium hydroxide, sodium hydroxide, sodium hydride, or a base which provides an alkoxy anion, hydrogen anion, or hydroxyl anion.

16. The method for synthesizing an aromatic secondary or tertiary amine as described in claim 10, wherein the arylchloride has a structure of

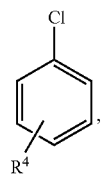

$R^4$ being an ortho-, meta-, or para-substituted alkyl, alkoxy, or hydrogen.

17. The method for synthesizing an aromatic secondary or tertiary amine as described in claim 10, wherein the organic amine is an $R^8,R^9$-substituted organic primary amine or secondary amine having a formula

$R^8$ being an alkyl, phenyl, or heterocyclic group; $R^9$ being an alkyl, phenyl, heterocyclic group, or hydrogen; the heterocyclic group being thiophene, furan, or pyridine.

* * * * *